the present invention relates to a paclitaxel composition and

(12) United States Patent
Chung et al.

(10) Patent No.: US 8,075,917 B2
(45) Date of Patent: Dec. 13, 2011

(54) COMPOSITION FOR SOLUBILIZATION OF PACLITAXEL AND PREPARATION METHOD THEREOF

(75) Inventors: Hesson Chung, Incheon (KR); Seo-Young Jeong, Gyeonggi-Do (KR); Ick-Chan Kwon, Seoul (KR); Yeong-Taek Park, Gyeonggi-Do (KR); In-Hyun Lee, Seoul (KR); Soon-Hong Yuk, Daejeon (KR); Young-Wook Choi, Seoul (KR); Jae-Hyung Park, Seoul (KR); Jin-Wook Chung, Seoul (KR)

(73) Assignee: Daehwa Pharm. Co., Ltd., Gangwon-Do (KR)

( * ) Notice: Subject to any disclaimer, the term of this patent is extended or adjusted under 35 U.S.C. 154(b) by 1049 days.

(21) Appl. No.: 10/521,669

(22) PCT Filed: Jul. 18, 2003

(86) PCT No.: PCT/KR03/01427
§ 371 (c)(1),
(2), (4) Date: Nov. 8, 2005

(87) PCT Pub. No.: WO2004/009075
PCT Pub. Date: Jan. 29, 2004

(65) Prior Publication Data
US 2006/0104999 A1    May 18, 2006

(30) Foreign Application Priority Data
Jul. 20, 2002    (KR) .................... 10-2002-0042791

(51) Int. Cl.
| | |
|---|---|
| A61K 7/00 | (2006.01) |
| A61K 8/02 | (2006.01) |
| A61K 9/14 | (2006.01) |
| A61K 47/00 | (2006.01) |
| A61K 31/04 | (2006.01) |
| A61K 31/15 | (2006.01) |
| A01N 25/00 | (2006.01) |
| A01N 33/18 | (2006.01) |
| A01N 33/24 | (2006.01) |
| A01N 27/00 | (2006.01) |

(52) U.S. Cl. ........ 424/489; 424/401; 514/741; 514/765; 514/786

(58) Field of Classification Search .................. None
See application file for complete search history.

(56) References Cited

U.S. PATENT DOCUMENTS
| | | | |
|---|---|---|---|
| 6,531,139 B1 * | 3/2003 | Gao et al. .......... | 424/400 |
| 6,538,019 B1 | 3/2003 | Nakajima et al. | |
| 2003/0059470 A1 * | 3/2003 | Muller ............ | 424/489 |
| 2006/0127420 A1 * | 6/2006 | Chung et al. ......... | 424/400 |
| 2006/0134144 A1 * | 6/2006 | Chung et al. ......... | 424/400 |
| 2006/0210622 A1 | 9/2006 | Pace et al. | |

FOREIGN PATENT DOCUMENTS

| | | |
|---|---|---|
| JP | 56-18914 A | 2/1981 |
| JP | 62-294612 A | 12/1987 |
| JP | 4-217912 A | 8/1992 |
| JP | 6-509577 T | 10/1994 |
| JP | 8-512301 A | 12/1996 |
| JP | 8-512303 A | 12/1996 |
| JP | 10-503750 A | 4/1998 |
| JP | 2001-524990 A | 4/2001 |
| JP | 2001-269115 A | 10/2001 |
| JP | 2002-080399 A | 3/2002 |
| JP | 2002-511099 A | 4/2002 |
| JP | 2004-520398 T | 7/2004 |
| WO | WO-93/02665 A1 | 2/1993 |
| WO | WO-00/59482 A1 | 10/2000 |
| WO | WO-00/74653 A1 | 12/2000 |
| WO | WO 01/01960 | 1/2001 |
| WO | WO-01/21154 A2 | 3/2001 |
| WO | WO 01/68139 | 9/2001 |
| WO | WO-01/68139 | 9/2001 |
| WO | WO-01/72299 A1 | 10/2001 |
| WO | WO 02/13815 | 2/2002 |
| WO | WO 02/13815 A1 * | 2/2002 |
| WO | WO-02/056878 A2 | 7/2002 |
| WO | WO 02/064132 | 8/2002 |
| WO | WO-02/64132 A2 | 8/2002 |
| WO | WO 03/045357 | 6/2003 |
| WO | WO-03/053350 A2 | 7/2003 |

OTHER PUBLICATIONS

Sparreboom, et al., "Limited oral bioavailability and active epithelial excretion of paclitaxel (Taxol) caused by P-glycoprotein in the intestine" *Proc. Natl. Acad. Sci. USA* 94:2031-2035 (Mar. 1997). Database WPI Week 200213, Thomson Scientific, London, UK; AN 2002-192770, XP002550012.

\* cited by examiner

*Primary Examiner* — Robert A Wax
*Assistant Examiner* — Jeffrey T Palenik
(74) *Attorney, Agent, or Firm* — Birch, Stewart, Kolasch & Birch, LLP (57) ABSTRACT

The present invention relates to a paclitaxel composition and the preparation methods thereof to solubilize paclitaxel wherein said composition comprises 4 to 90% by weight of at least one selected from the monoglycerides, 0.01 to 90% by weight of at least one oil and 0.01 to 20% by weight of paclitaxel. Also the present invention relates to a paclitaxel composition including emulsifiers and the preparation methods thereof to solubilize paclitaxel wherein said composition comprises 4 to 90% by weight of at least one selected from the monoglycerides, 0.01 to 90% by weight of at least one emulsifier and 0.01 to 20% by weight of paclitaxel. The composition of the present invention is an effective paclitaxel delivery system since the composition solubilizes paclitaxel, does not form aggregates after being dispersed in water, adsorbs well on the intestinal wall, and therefore has high bioavailability.

16 Claims, 3 Drawing Sheets

COMPOSITION FOR SOLUBILIZATION OF PACLITAXEL AND PREPARATION METHOD THEREOF

TECHNICAL FIELD

The present invention relates to a paclitaxel composition and the preparation methods thereof to solubilize paclitaxel.

BACKGROUND ART

Paclitaxel, an anticancer agent, shows excellent cytotoxicity to various kinds of cancers such as ovarian cancer, breast cancer, esophagus cancer, melanoma and leukemia. Paclitaxel formulation currently used in clinical remedies has been commercialized in the form of emulsion preconcentrate (self-emulsifying system) because its water solubility is very low even compared with an anti-cancer medicine of Bristol-Myers Squibb Company. Taxol® is a commercially available injection agent, in the form of solution, in which paclitaxel is mixed with solubilizing agent, that is, Cremophor EL (polyoxyethylene 35 castor oil, polyoxylethyaed castor oil and polyoxyethoxylated castor oil) in dehydrated alcohol (U.S. Pat. No. 5,438,072). It is known, however, that this agent has a limitation in directions and dosage because solubilizing agent in Taxol® causes toxic side effects. Therefore, many studies have been performed to develop new paclitaxel formulations with high stability and low toxic effects. There are many patents describing lipid emulsion, polymeric micelles and liposome. In emulsion formulation, not only emulsion using conventional oils and emulsifiers but also solid lipid nanoparticles, emulsion concentrate and so on have been patented. Also other solubilization techniques by utilizing liposome, polymeric nanoparticles and polymeric micelles have been developed. These formulations solubilizing paclitaxel took advantage of the accumulated technological advancement already developed for other insoluble drugs.

Also, even though paclitaxel is currently used to treat metastatic ovarian cancer and breast cancer, it is expected to be prescribed for various cancers, especially the metastatic solid tumors (e.g., lung cancer and hepatoma) in the near future. Therefore, market forecast is promising for paclitaxel.

From the pharmaceutical point of view, Taxol®, the most frequently prescribed paclitaxel formulation has a problem of forming precipitation when diluted inside the infusion bag due to the low solubility. In-line filter is used to prevent the precipitation from entering the blood stream of the patient. The exact dose of paclitaxel, therefore, is unknown and varies from time to time. Also, the plasticizer is known to leak out from the infusion bag made of PVC causing potential health problem. From the pharmacological point of view, Cremophor EL, the excipient can cause severe side-effects such as hypersensitivity, vasodilation, dyspnea, enervation and high blood pressure. From the pharmaceutical and pharmacological points of view, the stability and the safety of the drug must be improved by developing other administration routes and formulations.

The most promising and convenient administration route is considered to be the oral route. There is a big hurdle to overcome, however, since paclitaxel is not absorbed into the body due to the efflux mechanism by p-glycoprotein which exists in the epithelial cell of gastrointestinal tract. Many p-glycoprotein inhibitors are known up to date including cinchonin, calcium channel blockers such as verapamil and dihydropyridines (for instance nifedipine, nicardipine and nitrendipine), calmodulin antagonist such as trifluoroperazine, antihypertensive such as reserpine, Vinca alkaloids such as vincristine and vinblastine, steroids such as progesterone, antiarrythmics such as amiodarone and quinidine, anthelmintic such as quinacrine and quinine, and immunosuppressants such as cyclosporine A, staurosporine and tacrolimus.

In addition to the increased oral bioavailability of paclitaxel, the p-glycoprotein inhibitors can help overcome multidrug resistance by inhibiting p-glycoprotein existing in the cancer cells. On the other hand, paclitaxel is known to be metabolized by hepatic microsomal enzyme. Paclitaxel converts to 6-α-hydroxypaclitaxel and 3'-p-hydroxypaclitaxel by CYP2C8 and CYP3A4, respectively.

Cyclosporin A inhibits the formation of 6-α-hydroxypaclitaxel. Doxorubicin, etoposide (VP-16) and cisplatin inhibit the formation of 3'-p-hydroxypaclitaxel. And verapamil and tamoxifen inhibit the metabolism of paclitaxel to 6-α-hydroxypaclitaxel and 3'-p-hydroxypaclitaxel. Therefore, co-administration of paclitaxel with the above mentioned metabolism inhibitors could also increase the bioavailability of paclitaxel.

Many formulations have been developed to solubilize paclitaxel. One of the most widely used and successful formulations is Taxol®. Lipid emulsion (U.S. Pat. No. 6,391,832 Medical emulsion for lubrication and delivery of drugs; U.S. Pat. No. 6,348,491 Oil-in-water emulsion for encapsulating paclitaxel) or pre-concentrate which forms transparent colloidal system in water (U.S. Pat. No. 6,267,985 Clear oil-containing pharmaceutical compositions; U.S. Pat. No. 6,294,192 Triglyceride-free compositions and methods for improved delivery of hydrophobic therapeutic agents) are also well known. In case of pre-concentrate, clear oil composition forms dispersion of very small particles whose absorbance at 400 nm is less than 0.3.

The above formulation is distinctly different from the composition for solubilization of paclitaxel in the present invention. The composition in the present invention is coarsely dispersed in water, and the absorbance at 400 nm is above 0.38 in all cases and between 1 and 4 in most cases. In other words, efforts have been made to prepare nano-sized particles or its pre-concentrate to solubilize paclitaxel in the existing inventions whereas the current invention discloses the composition that does not disperse well and does disperse to form particles of a few micrometers in size if it does. The merits of the composition of the present invention include that paclitaxel does not precipitate out in the dispersion while it is a high mucoadhesive in the intestine.

One of the main obstacles in commercializing oral paclitaxel formulations is the problem of forming paclitaxel precipitation upon dilution with body fluid. Even if the formulation is stable before dilution, precipitation forms with time in the dispersion. Paclitaxel precipitation cannot be absorbed into the body in the intestine at all. Once the problem of precipitation formation is solved, however, another obstacle, efflux system of p-glycoprotein in the gastrointestinal tract, awaits lowering bioavailability of paclitaxel.

In the present invention, a mucoadhesive lipid, monoolein was used as a main component for oral delivery of paclitaxel. Even though paclitaxel is solubilized in monoolein, it forms precipitation in the cubic phase of the monoolein/water system. Therefore, we prepared an oily composition that does not form paclitaxel precipitation with time even after the composition is mixed with water. The cubic phase of the monoolein/water system is composed of ca. 60% (v/v) of water. On the other hand, when more than 10% of oil is added to monoolein, the mixture does not form cubic phase, but forms an amorphous composition that contains ca. 5~10% of water. It is worthwhile to note that this composition does not form paclitaxel precipitation. Also, this composition is very mucoadhesive to intestinal wall.

To date, oral paclitaxel formulation that does not require p-glycoprotein inhibitor has not been developed. Also the bioavailability of the oral paclitaxel formulations was very low even when it is co-administered with p-glycoprotein inhibitor orally.

To overcome the problem of forming paclitaxel precipitation in contact with water and of low oral bioavailability as mentioned above, the present invention provides mucoadhesive compositions for solubilization of paclitaxel that have high bioavailability when administered alone or with p-glycoprotein inhibitor and the preparation method thereof.

DETAILED DESCRIPTION OF THE INVENTION

The present invention provides compositions for solubilization of paclitaxel that is stable for a prolonged period, mucoadhesive, and highly bioavailable and the preparation method thereof.

More specifically, the present invention provides compositions for solubilization of paclitaxel including at least one monoglyceride, at least one oil and paclitaxel and the preparation method thereof.

Also, the present invention provides compositions for solubilization of paclitaxel including at least one monoglyceride, at least one oil, at least one emulsifier and paclitaxel and the preparation method thereof.

In what follows, the present invention will be described in detail.

The present invention provides compositions for solubilization of paclitaxel.

Specifically, the above composition is composed of 4~90% by weight of at least one selected from the monoglycerides, 0.01~90% by weight of at least one oil ad 0.01~20% by weight of paclitaxel (with respect to the total weight of the composition).

The above composition can be prepared by mixing at least one monoglyceride, at least one oil and paclitaxel at room or elevated temperature.

The above monoglycerides are selected from a group consisting of one or more saturated or unsaturated monoglycerides having 10~22 carbon atoms in the hydrocarbon chain. Monoglyceride is selected preferably from a group consisting of monoolein, monopalmitolein, monomyristolein, monoelaidin and monoerucin, and from a group consisting of the mixture of monoglycerides semi-synthesized from triglycerides of vegetable or animal oil, and more preferably monoolein.

The above oil is selected preferably from a group consisting of triglycerides, iodinated oil and vegetable or animal oil that can solubilize paclitaxel.

The above triglycerides are selected from a group consisting of one or more saturated or unsaturated triglycerides having 2~20 carbon atoms in the hydrocarbon chain. For instance, triacetin, tributyrin, tricaproin, tricaprylin, tricaprin or triolein can be used.

The above iodized oils include iodized poppy seed oil such as Lipiodol, Ethiodol and iodized soybean oil.

The above vegetable oils include soybean oil, cottonseed oil, olive oil, poppyseed oil, linseed oil or sesame oil.

The above animal oils include squalane or squalene.

Also, the above composition can additionally include other additives up to 5% by weight. For instance, the composition can further comprise alcohol, polyol or Cremophor to improve the solubility of paclitaxel, tocopherol or tocopherol acetate to prevent oxidation, fatty acid, fatty acid ester or fatty acid alcohol to increase drug absorption, and other insoluble drugs to achieve synergistic effect.

The above insoluble drugs include other anticancer drugs, p-glycoprotein inhibitors or hepatic metabolism blockers.

The above other anticancer drugs include doxorubicin, cisplatin, carboplatin, carmustin (BCNU), dacarbazine, etoposide, 5-fluorouracil or paclitaxel derivatives. The above paclitaxel derivatives include docetaxel, bromotaxel and taxotere.

The above p-glycoprotein inhibitors include cinchonin, calcium channel blocker, calmodulin antagonist, Vinca alkaloid, antiarrhythmic, steroid, antihypertension drug, anthelmintic or immunosuppressant. The above calcium channel blockers include dihydropyridines such as verapamil, nifedipine, nicardipine or nitrendipine. The above calmodulin antagonists include trifluoroperazine. The above antihypertension drugs include reserpine. The above Vinca alkaloids include vincristine or vinblastine. The above steroids include progesterone. The above antiarrhythmics include amiodarone and quinidine. The above anthelmintics include quinacrine and quinine. The above immunosuppressants include cyclosporins, staurosporin and tacrolimus The above hepatic metabolism blockers include anticancer drugs such as cyclosporin A, doxorubicin, etoposide (VP-16), cisplatin, verapamil and tamoxifen.

The compositions for solubilization of paclitaxel according to the present invention can be administered via various routes including oral administration, buccal administration, mucosal administration, nasal administration, intraperitoneal administration, subcutaneous injection, intramuscular injection, transdermal administration, intratumoral administration, and more preferably an oral administration.

The method of preparing the above composition for solubilization of paclitaxel comprises the steps of;
1) preparing the viscous liquid by solubilizing 4~90% by weight of at least one monoglyceride compound in 0.01~90% by weight of at least one oil by heating to below 50° C. (step 1); and
2) preparing homogeneous mixture by solubilizing completely 0.01~20% by weight of paclitaxel in said mixture in step (1) (step 2).

The mixture can be heated to 50° C. and sonicated in a bath type sonicator in step (2) to speed up the solubilization process.

Also, the method of preparing the above composition for solubilization of paclitaxel comprises the steps of;
1) mixing 4~90% by weight of at least one monoglyceride compound, 0.01~90% by weight of at least one oil and 0.01~20% by weight of paclitaxel (step 1); and
2) preparing homogeneous mixture by solubilizing completely the said mixture in step (1) (step 2).

The above mixture can be heated to 50° C. and sonicated in a bath type sonicator or stirred in step (2) to speed up the solubilization process.

The preparation methods described above are only two of many possible methods, and other preparation methods can also be used to obtain the above composition for solubilization of paclitaxel.

Also, the present invention provides the compositions for solubilization of paclitaxel including emulsifiers.

More particularly, the above composition is composed of 4~90% by weight of at least one selected from the monoglycerides, 0.01~90% by weight of at least one oil, 0.01~90% by weight of at least one emulsifier and 0.01~20% by weight of paclitaxel (with respect to the total weight of the composition).

The above composition can be prepared by adding at least one monoglyceride, at least one oil, at least one emulsifier and paclitaxel at room or elevated temperature.

The above monoglycerides are selected from a group consisting of one or more saturated or unsaturated monoglycerides having 10~22 carbon atoms in the hydrocarbon chain. Monoglyceride is selected preferably from a group of consisting of monoolein, monopalmitolein, monomyristolein, monoelaidin, and monoerucin, or from a group consisting of monoglycerides semi-synthesized from triglycerides of vegetable or animal oils or their mixture, and more preferably monoolein.

The above oil is selected preferably from a group consisting of triglycerides, iodinated oil and vegetable or animal oil that can solubilize paclitaxel.

The above triglycerides are selected from a group consisting of one or more saturated or unsaturated triglycerides having 2~20 carbon atoms in the hydrocarbon chain. For instance, triacetin, tributyrin, tricaproin, tricaprylin, tricaprin or triolein can be used.

The above iodized oils include iodized poppy seed oil such as Lipiodol, Ethiodol and iodized soybean oil.

The above vegetable oils include soybean oil, cottonseed oil, olive oil, poppyseed oil, linseed oil or sesame oil.

The above animal oils include squalane or squalene.

The above emulsifier is preferred to select from the group consisting of a phospholipid, a non-ionic surfactant, an anionic surfactant, a cationic surfactant, and bile acid.

The phospholipid is preferred to select from the group consisting of a phosphatidylcholine (PC) and its derivative, a phosphatidylethanolamine (PE) and its derivative, a phosphatidylserine (PS) and its derivative, and a polymeric lipid wherein a hydrophilic polymer is conjugated to the lipid headgroup.

The non-ionic surfactant is selected from the group consisting of a poloxamer (also known as Pluronic: polyoxyethylene-polyoxypropylene copolymer), a sorbitan ester (Span), a polyoxyethylene sorbitan (Tween) and a polyoxyethylene ether (Brij).

The anionic surfactant is selected from the group consisting of a phosphatidylserine (PS) and its derivative, a phosphatidic acid (PA) and its derivative and sodium dodecyl sulfate (SDS).

The cationic surfactant is selected from the group consisting of 1,2-dioleyl-3-trimethylammonium propane (DOTAP), dimethyldioctadecylammonium bromide (DDAB), N-[1-(1, 2-dioleyloxy)propyl]-N,N,N-trimethylammonium chloride (DOTMA), 1,2-dioleyl-3-ethylphosphocholine (DOEPC) and 3β-[N-[(N',N'-dimethylamino)ethan]carbamoyl]cholesterol (DC-Chol).

The bile acid is selected from the group consisting of cholic acid, its salt and derivatives; deoxycholic acid, its salt and derivatives; chenocholic acid, its salt and derivatives; and lithocholic acid, its salt and derivatives.

Other additives can be added to the above to be within 5% by weight. For instance, the composition can further comprise alcohol, polyol or Cremophor to improve the solubility of paclitaxel, tocopherol or tocopherol acetate to prevent oxidation, and fatty acid, fatty acid ester or fatty acid alcohol to increase drug absorption. Depending on the symptom, other insoluble drug can also be added in the composition including emulsifier according to the present invention.

The above insoluble drugs include other anticancer drugs, p-glycoprotein inhibitors or hepatic metabolism blocker.

The above other anticancer drugs include doxorubicin, cisplatin, carboplatin, carmustin (BCNU), dacarbazine, etoposide, 5-fluorouracil or paclitaxel derivatives. The above paclitaxel derivatives include docetaxel, bromotaxel and taxotere.

The above p-glycoprotein inhibitors include cinchonin, calcium channel blocker, calmodulin antagonist, Vinca alkaloid, antiarrhythmic, steroid, antihypertension drug, anthelmintic or immunosuppressant. The above calcium channel blockers include dihydropyridines such as verapamil, nifedipine, nicardipine or nitrendipine. The above calmodulin antagonists include trifluoroperazine. The above antihypertension drugs include reserpine. The above Vinca alkaloids include vincristine or vinblastine. The above steroids include progesterone. The above antiarrhythmics include amiodarone and quinidine. The above anthelmintics include quinacrine and quinine. The above immunosuppressants include cyclosporins, staurosporin and tacrolimus The above hepatic metabolism blockers include anticancer drugs such as cyclosporin A, doxorubicin, etoposide (VP-16), cisplatin, verapamil and tamoxifen.

The compositions for solubilization of paclitaxel including emulsifiers according to the present invention can be administered via various routes including oral administration, buccal administration, mucosal administration, nasal administration, intraperitoneal administration, subcutaneous injection, intramuscular injection, transdermal administration, intratumoral administration, and more preferably an oral administration.

The method of preparing the above composition for solubilization of paclitaxel including emulsifiers comprises the steps of;
  1) preparing the viscous liquid by mixing 4~90% by weight of at least one monoglyceride compound, 0.01~90% by weight of at least one oil, and 0.01~90% by weight of at least one emulsifier by heating to below 50° C. (step 1); and
  2) preparing homogeneous mixture by solubilizing completely 0.01~20% by weight of paclitaxel in said mixture in step (1) (step 2).

One of the examples in preparing the composition for solubilization of paclitaxel including emulsifiers is as follows. In homogeneous viscous liquid obtained by mixing monoglyceride, oil and emulsifier by heating to below 50° C., paclitaxel is added. The mixture was stirred or sonicated for 3~5 minutes at or below 50° C. to obtain homogeneous composition.

The method of preparing the above composition for solubilization of paclitaxel including emulsifiers can also comprise the steps of;
  1) preparing the paclitaxel solution by solubilizing 0.01~20% by weight of paclitaxel in 0.01~90% by weight of at least one oil by sonicating in a bath type sonicator (step 1); and
  2) preparing homogeneous mixture by mixing the paclitaxel solution in step (1) and 0.01~90% by weight of at least one emulsifier and 4~90% by weight of monoglyceride (step 2).

The preparation methods described above are only two of many possible methods, and other preparation method can also be used to obtain the above composition for solubilization of paclitaxel including emulsifier.

The formulations of the present invention in viscous liquid, gel or semi-solid form are stable for a long period of time since the physical property of the composition does not change and the components including paclitaxel do not degrade with time. Also the compositions for solubilization of paclitaxel of the present invention is an efficient solubilization system since they can be easily dispersed in water or in aqueous solutions to become particles bigger than 400 nm in diameter, and the dispersion does not form aggregates with time. Also the absorbance of the dispersion ranges 1 and 4 at the wavelength of 400 nm indicating that the average particle size is relatively big.

In other words, the composition of the present invention does not form fine dispersion with nano-sized particles, but form coarse dispersion with the particles of several hundred nanometers to several micrometers in size. The dispersion of the composition of the present invention does not form paclitaxel aggregate with time. When administered into the body, the composition is highly mucoadhesive and adheres onto a wide area of intestinal wall. Paclitaxel in the composition is absorbed through the mucosal membrane in the intestine since mucoadhesive monoolein can be absorbed without further metabolization process.

BEST MODE FOR CARRYING OUT THE INVENTION

This invention is explained in more detail based on the following Examples but they should not be construed as limiting the scope of this invention.

Buffer solutions used in the present invention are as follows:

Plate Well Coating Buffer: 50 mM Sodium Phosphate, 0.15 M NaCl and 0.02% sodium azide, pH 7.0 (PBS), Plate Well Blocking Buffer: PBS containing 1% (w/v) Bovine Serum Albumin (BSA), Sample Diluting Buffer: PBS containing 0.25% (w/v) BSA, 0.05% (v/v) Tween-20, 20% (v/v) Methanol and 0.02% sodium azide (PBSTM), Antibody Diluting Buffer: PBS containing 0.25% (w/v) BSA, 0.05% (v/v) Tween-20 and 0.02% sodium azide (PBST), Wash Buffer: 50 mM Tris HCl, pH 7.0, 0.15 M NaCl, containing 0.05% (v/v) Tween 20 and 0.02% sodium azide (TBST), Enzyme Substrate Buffer: 25 mM Tris, pH 9.5, 0.15 M NaCl containing 5 mM MgCl2 and 0.02% (w/v) sodium azide.

Example 1

Composition for Solubilization of Paclitaxel According to the Change in the Composition Ratio (1)

(1) Manufacturing Composition for Solubilization of Paclitaxel

Viscous oily solution was prepared by mixing 1 g monoolein and 0.5 g tricaprylin and warmed at 40° C. Fifteen milligrams of paclitaxel was added into the oily solution and sonicated in a bath type sonicator for complete solubilization to obtain a liquid formulation.

(2) Property Analysis of Thus Prepared Composition for Solubilization of Paclitaxel The size of the emulsion particles were measured by using Malvern Zetasizer (Malvern Instruments Limited, England) after diluting the emulsion by adding 3 mL of distilled water with 2 μL of thus obtained liquid formulation. An average particle size and polydispersity was obtained by measuring a given formulation three times (Orr, *Encyclopedia of emulsion technology*, 1, 369-404, 1985). The polydispersity was obtained as the variance indicated by the logarithmic scale in the logarithmic normal distribution function. This method was used in measuring the particle size and the polydispersity throughout the following Examples.

The above composition exists as semi-solid or solid at room temperature and in the refrigerator, respectively, but as liquid at or above 40° C. Paclitaxel precipitation was not observed under polarized light microscope, and phase separation was not observed either. Unstable dispersion with the average particle size of 1230 nm was obtained when the above composition was vortexed for 10 s in water. Paclitaxel precipitation was not observed under polarized light microscope 24 hour after preparing the dispersion.

Example 2

Composition for Solubilization of Paclitaxel According to the Change in the Composition Ratio (2)

Viscous oily solution was prepared by mixing 1 g monoolein and 0.5 g tricaprylin and warmed at 40° C. Thirty milligrams of paclitaxel was added into the oily solution and sonicated in a bath type sonicator for complete solubilization. The above composition exists as semi-solid or solid at room temperature and in the refrigerator, respectively, but as liquid at or above 40° C. Paclitaxel precipitation was not observed under polarized light microscope, and phase separation was not observed either. Unstable dispersion with the average particle size of 2080 nm was obtained when the above composition was vortexed for 10 s in water. Paclitaxel precipitation was not observed under polarized light microscope 24 hour after preparing the dispersion.

The results of the Examples 1 and 2 are summarized in the following Table 1.

TABLE 1

| Content (weight %) | | | Particle size (nm) | |
|---|---|---|---|---|
| Monoolein | Tricaprylin | Paclitaxel | (polydispersity) | Example |
| 66 | 33 | 1 | 1230 (0.200) | 1 |
| 65 | 33 | 2 | 2080 (1.000) | 2 |

Example 3

Composition for Solubilization of Paclitaxel Including Emulsifiers According to the Change in the Composition Ratio (1)

Viscous oily solution was prepared by mixing completely 1 g monoolein, 0.5 g tricaprylin and 0.3 g of Tween 80, and warmed at 40° C. Eighteen milligrams of paclitaxel was added into the oily solution and sonicated in a bath type sonicator for complete solubilization. Dispersion with the average particle size of 600 nm was obtained when the above composition was vortexed for 10 s in water. Paclitaxel precipitation was not observed under polarized light microscope 24 hour after preparing the dispersion. The above composition exists as semi-solid or solid at room temperature and in the refrigerator, respectively, but as liquid at or above 40° C.

Example 4

Composition for Solubilization of Paclitaxel Including Emulsifiers According to the Change in the Composition Ratio (2)

The composition and dispersed liquid were prepared the same as those of the Example 1 with the exception that 1 g monoolein, 1 g tricaprylin, 0.4 g of Tween 80 and 10 mg of paclitaxel were used, and their particle size and polydispersity were measured by the same methods in the Example 1. Dispersion with the average particle size of 530 nm was obtained. Paclitaxel precipitation was not observed under polarized light microscope, and phase separation was not observed either. The above composition exists as semi-solid or solid at room temperature and in the refrigerator, respectively, but as liquid at or above 40° C.

The results of the Examples 3 and 4 are summarized in the following Table 2.

TABLE 2

| Content (weight %) | | | | Particle size (nm) | |
|---|---|---|---|---|---|
| Mono-olein | Tricapry-lin | Tween 80 | Paclitaxel | (polydispersity) | Example |
| 55 | 28 | 16 | 1 | 600 (0.200) | 3 |
| 41.5 | 41.5 | 16.6 | 0.4 | 530 (1.000) | 4 |

Comparative Example 1

Composition Including Emulsifier for Solubilization of Paclitaxel without Oil (1)

The composition and dispersed liquid were prepared the same as those of the Example 1 with the exception that 1 g monoolein, 0.2 g of Tween 80 and 12 mg of paclitaxel were used, and their particle size and polydispersity were measured by the same methods in the Example 1. Dispersion with the average particle size of 700 nm was obtained. Paclitaxel precipitation was observed under polarized light microscope, and the dispersion became unstable 1 hour after preparation.

Comparative Example 2

Composition Including Emulsifier for Solubilization of Paclitaxel without Oil (2)

The composition and dispersed liquid were prepared the same as those of the Example 1 with the exception that 1 g monoolein, 0.24 g of Pluronic F-68 and 12.4 mg of paclitaxel were used, and their particle size and polydispersity were measured by the same methods in the Example 1. Dispersion with the average particle size of 640 nm was obtained. Paclitaxel precipitation was observed under polarized light microscope, and the dispersion became unstable 1 hour after preparation.

Comparative Example 3

Composition Including Emulsifier for Solubilization of Paclitaxel without Monoolein (1)

The composition and dispersed liquid were prepared the same as those of the Example 1 with the exception that 1 g tricaprylin, 0.2 g of Tween 80 and 12 mg of paclitaxel were used, and their particle size and polydispersity were measured by the same methods in the Example 1. Dispersion with the average particle size of 560 nm was obtained. Paclitaxel precipitation was not observed under polarized light microscope, and phase separation was not observed either.

Example 5

Composition for Solubilization of Paclitaxel Including Emulsifiers According to the Change in the Oil (1)

The composition and dispersed liquid were prepared the same as those of the Example 1 with the exception that 1 g monoolein, 0.5 g tributyrin, 0.3 g of Tween 80 and 18 mg of paclitaxel were used and their particle size and polydispersity were measured by the same methods in the Example 1. Dispersion with the average particle size of 950 nm was obtained. Paclitaxel precipitation was not observed under polarized light microscope, and phase separation was not observed either, 24 hours after preparing the dispersion. The above composition exists as semi-solid or solid at room temperature and in the refrigerator, respectively, but as liquid at or above 40° C.

Example 6

Composition for Solubilization of Paclitaxel Including Emulsifiers According to the Change in the Oil (2)

The composition and dispersed liquid were prepared the same as those of the Example 1 with the exception that 1 g monoolein, 0.5 g lipiodol (Lipiodol Ultra-fluid, Laboratoire Guerbet, France, Iodine content: 38% by weight), 0.3 g of Tween 80 and 18 mg of paclitaxel were used and their particle size and polydispersity were measured by the same methods in the Example 1. Dispersion with the average particle size of 680 nm was obtained. Paclitaxel precipitation was not observed under polarized light microscope, and phase separation was not observed either, 24 hours after preparing the dispersion. The above composition exists as semi-solid or solid at room temperature and in the refrigerator, respectively, but as liquid at or above 40° C.

Example 7

Composition for Solubilization of Paclitaxel Including Emulsifiers According to the Change in the Oil (3)

The composition and dispersed liquid were prepared the same as those of the Example 1 with the exception that 1 g monoolein, 0.5 g squalane (Sigma Chemical Company), 0.3 g of Tween 80 and 18 mg of paclitaxel were used and their particle size and polydispersity were measured by the same methods in the Example 1. Dispersion with the average particle size of 598 nm was obtained. Paclitaxel precipitation was not observed under polarized light microscope, and phase separation was not observed either, 24 hours after preparing the dispersion. The above composition exists as semi-solid or solid at room temperature and in the refrigerator, respectively, but as liquid at or above 40° C.

Example 8

Composition for Solubilization of Paclitaxel Including Emulsifiers According to the Change in the Oil (4)

The composition and dispersed liquid were prepared the same as those of the Example 1 with the exception that 1 g monoolein, 0.5 g safflower seed oil (Sigma Chemical Company), 0.3 g of Tween 80 and 18 mg of paclitaxel were used and their particle size and polydispersity were measured by the same methods in the Example 1. Dispersion with the average particle size of 1040 nm was obtained. Paclitaxel precipitation was not observed under polarized light microscope, and phase separation was not observed either, 24 hours after preparing the dispersion. The above composition exists as semi-solid or solid at room temperature and in the refrigerator, respectively, but as liquid at or above 40° C.

The results of the Examples 5-8 are summarized in the following Table 3.

TABLE 3

| Oil | Particle size (nm) (polydispersity) | Example |
| --- | --- | --- |
| Tributyrin | 950 (0.661) | 5 |
| Lipiodol | 680 (1.000) | 6 |
| Squalane | 597 (0.550) | 7 |
| Safflower seed oil | 1040 (0.497) | 8 |

*Monoolein:Oil:Tween 80:Paclitaxel = 55:28:16:1 (Weight ratio)

Example 9

Composition for Solubilization of Paclitaxel Including Emulsifiers According to the Change in the Paclitaxel Content (1)

The composition and dispersed liquid were prepared the same as those of the Example 1 with the exception that 1 g monoolein, 0.5 g tricaprylin, 0.3 g of Tween 80 and 38 mg of paclitaxel were used and their particle size and polydispersity were measured by the same methods in the Example 1. Dispersion with the average particle size of 1450 nm was obtained. Paclitaxel precipitation was not observed under polarized light microscope, and phase separation was not observed either, 24 hours after preparing the dispersion. The above composition exists as semi-solid or solid at room temperature and in the refrigerator, respectively, but as liquid at or above 40° C.

Example 10

Composition for Solubilization of Paclitaxel Including Emulsifiers According to the Change in the Paclitaxel Content (2)

The composition and dispersed liquid were prepared the same as those of the Example 1 with the exception that 19 monoolein, 0.5 g tricaprylin, 0.3 g of Tween 80 and 54 mg of paclitaxel were used and their particle size and polydispersity were measured by the same methods in the Example 1. Dispersion with the average particle size of 1630 nm was obtained. Paclitaxel precipitation was not observed under polarized light microscope, and phase separation was not observed, 24 hours after preparing the dispersion. Unlike other compositions in Examples 1~7, the above composition exists as liquid or solid at room temperature and in the refrigerator, respectively.

The results of the Examples 9 and 10 are summarized in the following Table 4.

TABLE 4

| Content (weight %) | | | | | |
|---|---|---|---|---|---|
| Mono-olein | Tricapry-lin | Tween 80 | Paclitaxel | Particle size (nm) (polydispersity) | Example |
| 55 | 27 | 16 | 2 | 1450 (1.000) | 9 |
| 54 | 27 | 16 | 3 | 1630 (1.000) | 10 |

Example 11

Composition for Solubilization of Paclitaxel Including Emulsifiers According to the Change in the Emulsifier The composition and dispersed liquid were prepared the same as those of the Example 3 with the exception that Pluronic F68 (BASF Company) was used instead of Tween 80. Dispersion with the average particle size of 420 nm (polydispersity 0.284) was obtained. Paclitaxel precipitation was not observed under polarized light microscope, and phase separation was not observed either, 24 hours after preparing the dispersion. The above composition exists as semi-solid or solid at room temperature and in the refrigerator, respectively, but as liquid at or above 40° C.

Example 12

In Vivo Oral Administration of Composition for Solubilization of Paclitaxel (1)

Animal experiments were performed by using the composition for the solubilization of paclitaxel prepared in the above Example 1.

① Oral Administration of Composition for the Solubilization of Paclitaxel

One hundred microliters of the mucoadhesive formulation containing 1 mg paclitaxel was administered into Balb/C mouse (6~7 weeks old, female) fasted for 4 hours previously by using a gastric sonde. As a control group, 167 μl of Taxol® of Bristol-Myers Squibb Company dispersed in 0.5 ml of water (corresponding to 1 mg of paclitaxel) was administered orally. One hundred microliters of tricaprylin/Tween 80 composition without monoolein (containing 1 mg paclitaxel) prepared in Comparative Example 3 was used as another control group and administered orally. One, 2, 3 and 4 h after the oral administration of the compositions, the concentration of paclitaxel in the blood collected from the eye was determined.

As a control for oral administration, Taxol® of Bristol-Myers Squibb Company was administered intravenously into Balb/C mouse (6~7 weeks old, female), and the concentration of paclitaxel in blood was determined for 4 hours after intravenous injection. After dispersing 0.1 ml of Taxol® in 5.9 ml water, 0.1 ml of the dispersion (corresponding to 10 μg of paclitaxel) was administered by bolus injection into the tail vein of Balb/C mouse fasted for 4 hours. Blood was collected 0.5, 1, 2 and 4 h after the administration of the compositions, and the concentration of paclitaxel in the blood collected from the eye was determined.

② Determination of Total Concentration of Paclitaxel and its Metabolites in Blood (ELISA Method)

The total concentration of paclitaxel and its metabolites in blood was determined by using Anti-taxane monoclonal kit (Model number 8A10) from Hawaii Biotech Company. Paclitaxel is known to be converted to 6-α-hydroxypaclitaxel and 3'-p-hydroxypaclitaxel by CYP2C8 and CYP3A4, respectively. Various metabolites including the primary metabolites of paclitaxel exist in the blood. Anti-taxane monoclonal kit enables us to determine the concentration of paclitaxel and all of the metabolites containing taxane ring (Grothaus, G. P., Bignami, G. S., O'Malley, S., Harada, K. E., Byrnes, J. B., Waller, D. F., Raybould, T. J. G., Mcguire, M. T. and Alvaro, B., Taxane-specific monoclonal antibodies: measurement of Taxol, baccatin III, and 'total taxanes' in *Taxus brevifolia* extracts by enzyme immunoassay. J. Nat. Prod. 58, pp. 1003-1014, 1995).

The blood sample was serially diluted 4 times. Taxol-protein coating antigen (blue label) was diluted 100 times by phosphate buffered saline (PBS). After 100 μl of the diluted antigen solution was put into each well of the 96-well plate, the plate was incubated for 1 hour. After the plate was washed 4 times with TBST, it was blocked by adding PBS containing 1% bovine serum albumin for 1 hour. After each well was washed continuously four times with TBST, 50 μl of the serially diluted samples were put into each well. After diluting HBC Taxol Standard (RED label) serially with PBST, 50 μl of the diluted standard solution was put into each well. Fifty microliters of the antibody solution prepared by mixing 4.5 ml PBST and 50 μl of anti-taxane rabbit antibody (green label) was added in each well. After the wells were washed four times with TBST, 100 μl of secondary antibody solution diluted 1000 times with PBST was added and incubated for one hour. After washing the wells four times with TBST, 200

μl of pNPP solution at 1 mg/ml was added in each well. After incubating the plate for 1 hour at room temperature, the absorbance was measured at 414 nm by ELISA reader and compared with that at 690 nm for quantitative analysis.

Figure 1:
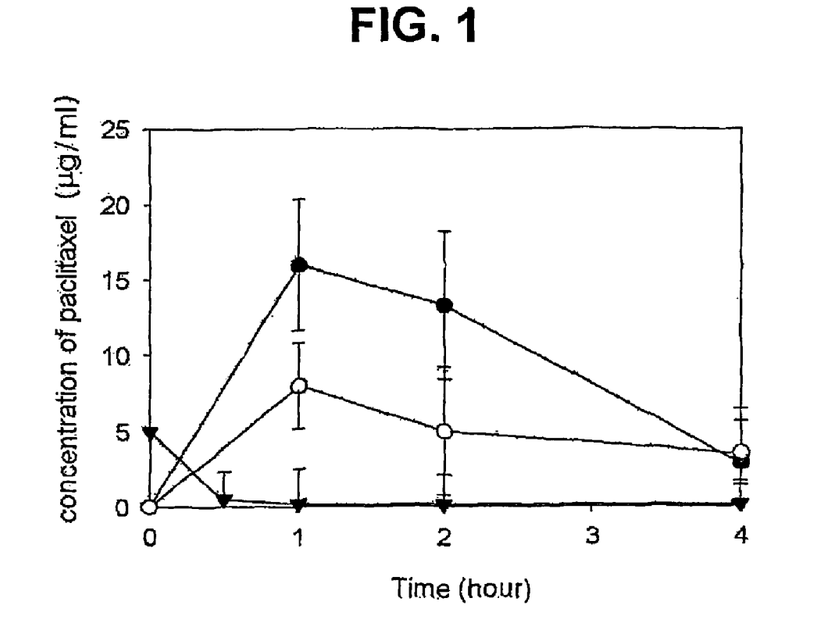
FIG. 1 is a graph showing the total concentration of paclitaxel and its metabolites in blood after oral administration of the liquid formulation solubilizing paclitaxel in Examples 1 and 2 of the present invention. The quantitative analysis of total concentration of paclitaxel and its metabolites was performed by ELISA. Taxol® of Bristol-Myers Squibb Company was administered via intravenous route as a control group.
—●—; a group orally administered with liquid formulation for solubilization of paclitaxel of the present invention (1 mg paclitaxel, weight ratio of the composition is monoolein:tricaprylin:paclitaxel=66:33:1, the composition in Example 1), and
—○—; a group orally administered with liquid formulation for solubilization of paclitaxel of the present invention (2 mg paclitaxel, weight ratio of the composition is monoolein:tricaprylin:paclitaxel=65:33:2, the composition in Example 2)
—▲—; a group intravenously administered with Taxol® of Bristol-Myers Squibb Company (10 μg paclitaxel).

③ Results of Oral Administration of Composition for the Solubilization of Paclitaxel The changes in the paclitaxel concentration in blood with time are shown in FIG. 1. When the bioavailability of paclitaxel upon bolus injection was set to 100%, the relative bioavailability upon oral administration of composition for the solubilization of paclitaxel was calculated by the following formula.

$$\text{Bioavailability}(\%) = \frac{AUCoral}{AUCiv} \times \frac{DOSEiv}{DOSEoral} \times 100$$

Wherein, AUCoral and AUCiv represent area under the curve after oral and intravenous administration, respectively, and DOSEiv and DOSEoral represent the paclitaxel dose for the oral and intravenous administration, respectively. The bioavailability upon oral administration of composition for the solubilization of paclitaxel when compared to the bolus injection was 19.5%.

Example 13

In Vivo Oral Administration of Composition for Solubilization of Paclitaxel (2)

Fifty microliters of the composition for solubilizing paclitaxel including emulsifier prepared in Example 2 containing 1 mg paclitaxel was administered into Balb/C mouse as in Example 12. As a control for oral administration, Taxol® of Bristol-Myers Squibb Company was administered intravenously (corresponding to 10 μg of paclitaxel/mouse). The total concentrations of paclitaxel and its metabolites in blood with time are determined by ELISA. FIG. 1 shows the result in comparison to that of Example 12. The bioavailability upon oral administration of composition for the solubilization of paclitaxel when compared to the bolus injection was 9.5±5%.

Example 14

Figure 2:
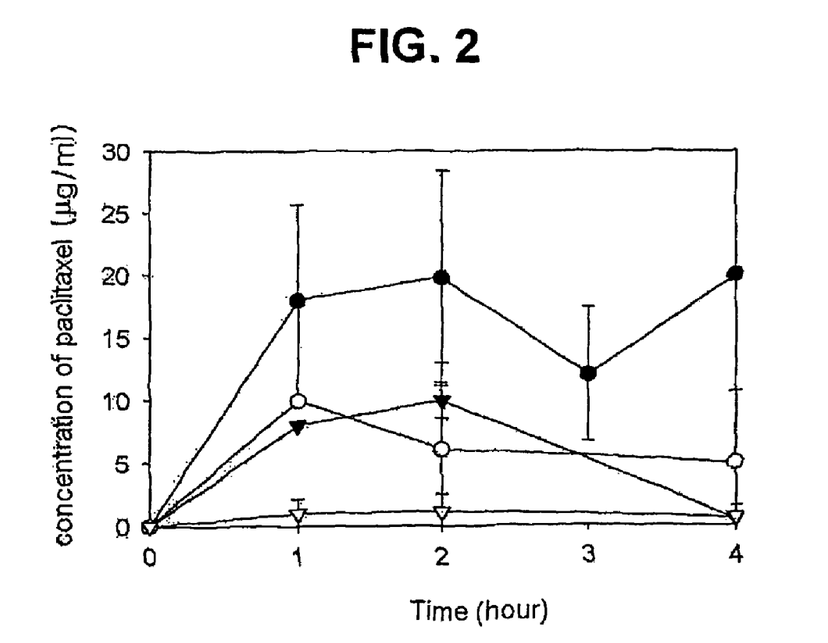
FIG. 2 is a graph showing the total concentration of paclitaxel and its metabolites in blood after oral administration of the liquid formulation containing emulsifier with different ratios of paclitaxel. The quantitative analysis of total concentration of paclitaxel and its metabolites was performed by ELISA. Taxol® of Bristol-Myers Squibb Company was administered orally as a control group.
—●—; a group orally administered with liquid formulation containing emulsifier for solubilization of paclitaxel of the present invention (1 mg paclitaxel, weight ratio of the composition is monoolein:tricaprylin:Tween 80:paclitaxel=55:28:16:1, the composition in Example 3),
—○—; a group orally administered with liquid formulation containing emulsifier for solubilization of paclitaxel of the present invention (1 mg paclitaxel, weight ratio of the composition is monoolein:tricaprylin:Tween 80:paclitaxel=54:27:16:2, the composition in Example 9),
—▲— a group orally administered with liquid formulation containing emulsifier for solubilization of paclitaxel of the present invention (1 mg paclitaxel, weight ratio of the composition is monoolein:tricaprylin:Tween 80:paclitaxel=55:27:16:3, the composition in Example 10), and
—□—; a group orally administered with Taxol® of Bristol-Myers Squibb Company (1 mg paclitaxel).

In Vivo Oral Administration of Composition for Solubilization of Paclitaxel Including Emulsifier—Effect of Paclitaxel Content The compositions for solubilizing paclitaxel including emulsifier prepared in Examples 3, 9 and 10 containing 1 mg paclitaxel were administered into Balb/C mouse by using identical method as in Example 12. As control groups, Taxol® of Bristol-Myers Squibb Company was administered orally (corresponding to 1 mg of paclitaxel) as well as intravenously (corresponding to 10 μg/mouse) as in Example 11. The total concentrations of paclitaxel and its metabolites in blood with time are determined by ELISA as shown in FIG. 2. The bioavailability calculated by setting that of Taxol® upon bolus injection in Example 12 to 100% is listed in Table 5. The bioavailability upon oral administration of composition for the solubilization of paclitaxel including emulsifier when compared to the bolus injection was approximately 10~30%. On the other hand, the bioavailability of orally administered Taxol® was 1.7±3%.

TABLE 5

| Oral formulation Content (weight %) | | | | Bioavail- | |
|---|---|---|---|---|---|
| Monoolein | Tricaprylin | Tween 80 | Paclitaxel | ability (%) | Example |
| 55 | 28 | 16 | 1 | 29.5 | 3 |
| 55 | 27 | 16 | 2 | 12.1 | 9 |
| 54 | 27 | 16 | 3 | 11.6 | 10 |

Example 15

Figure 3:
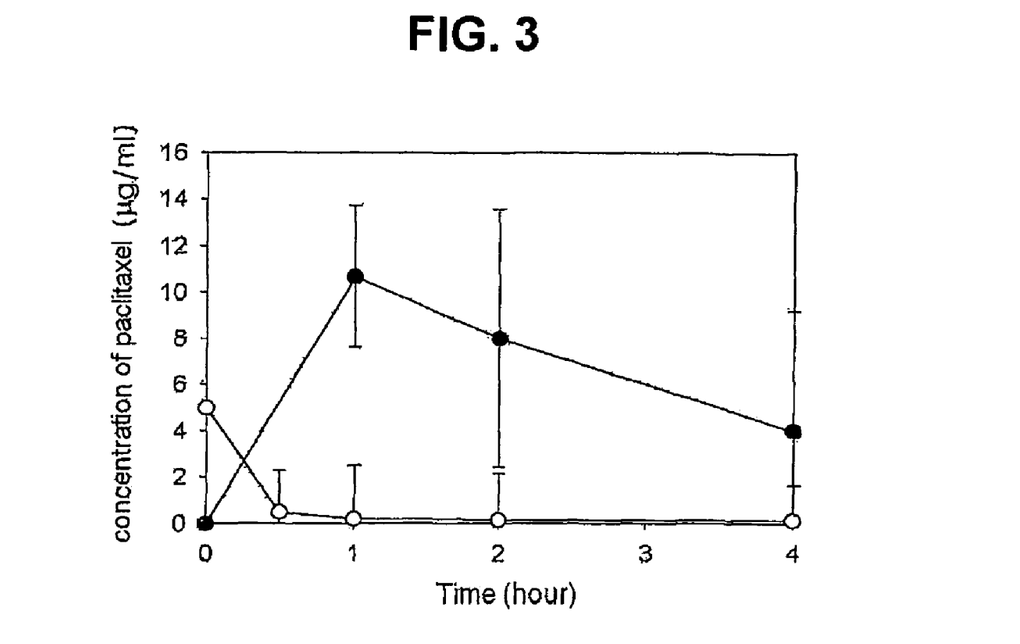
FIG. 3 is a graph showing the total concentration of paclitaxel and its metabolites in blood after oral administration of the liquid formulation containing emulsifier in Example 11 of the present invention. The quantitative analysis of total concentration of paclitaxel and its metabolites was performed by ELISA. Taxol® of Bristol-Myers Squibb Company was administered intravenously as a control group.
—●—; a group orally administered with liquid formulation containing emulsifier for solubilization of paclitaxel of the present invention (1 mg paclitaxel, weight ratio of the composition is monoolein:tricaprylin:Pluronic F68:paclitaxel=55:28:16:1, the composition in Example 11), and
—○—; a group intravenously administered with Taxol® of Bristol-Myers Squibb company (10 μg paclitaxel).

In Vivo Oral Administration of Composition for Solubilization of Paclitaxel Including Emulsifier—Effect of Emulsifier The compositions for solubilizing paclitaxel including emulsifier prepared in Example 11 containing 1 mg paclitaxel were administered into Balb/C mouse by using identical method as in Example 12. As a control group, Taxol® of Bristol-Myers Squibb Company was administered intravenously (corresponding to 10 μg/mouse). The total concentrations of paclitaxel and its metabolites in blood with time are determined by ELISA as shown in FIG. 3. The bioavailability upon oral administration of composition for the solubilization of paclitaxel including emulsifier when compared to the bolus injection was approximately 13.4±4%.

Example 16

Figure 4:
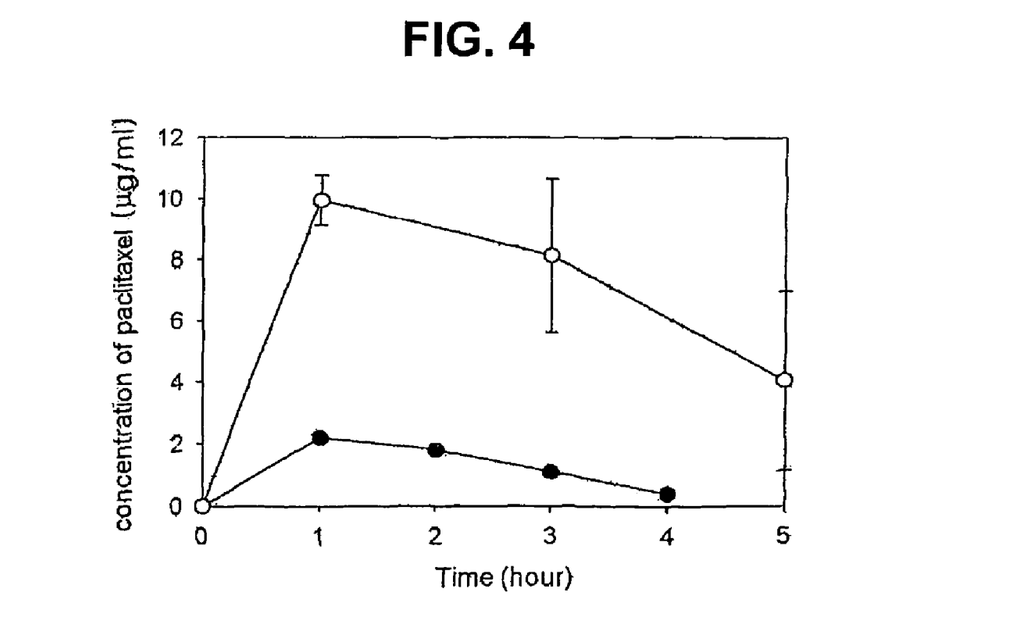
FIG. 4 is a graph showing the total concentration of paclitaxel and its metabolites in blood after oral administration of the liquid formulation containing emulsifier in Example 4 of the present invention with or without 1 mg of verapamil. The quantitative analysis of total concentration of paclitaxel and its metabolites was performed by ELISA.
—●—; a group orally administered with liquid formulation containing emulsifier for solubilization of paclitaxel of the present invention (1 mg paclitaxel, weight ratio of the composition is monoolein:tricaprylin:Pluronic F-68:paclitaxel=55:28:16:1, the composition in Example 4), and
—○—; a group orally administered with verapamil and liquid formulation containing emulsifier for solubilization of paclitaxel of the present invention (1 mg paclitaxel, weight ratio of the composition is monoolein:tricaprylin:Pluronic F68:paclitaxel=55:28:16:1, the composition in Example 4+1 mg verapamil).

In Vivo Oral Administration of Composition for Solubilization of Paclitaxel Including Emulsifier—Coadministration of Verapamil The composition for solubilizing paclitaxel including emulsifier prepared in Example 4 containing 1 mg paclitaxel were administered into Balb/C mouse by using identical method as in Example 12. Another group of mice were administered with the composition for solubilizing paclitaxel including emulsifier prepared in Example 4 containing 1 mg paclitaxel and 1 mg of verapamil. The total concentrations of paclitaxel and its metabolites in blood with time are determined by ELISA as shown in FIG. 4. The bioavailability upon oral administration of composition for the solubilization of paclitaxel including emulsifier when compared to the bolus injection of Taxol® in Example 12 was approximately 2.7%. When verapamil was co-administered, however, the oral bioavailability increased to 17.6%.

Example 17

In Vivo Oral Administration of Composition for Solubilization of Paclitaxel Including Emulsifier—Determination of Paclitaxel Concentration by HPLC The composition for solubilizing paclitaxel including emulsifier prepared in Example 3 containing 1 mg paclitaxel were administered into Balb/C mouse by using identical method as in Example 12. Paclitaxel concentration was determined by HPLC. When the above ELISA method was used, total concentration of paclitaxel as well as its metabolites is determined. HPLC analysis, however, detects intact paclitaxel molecule only in the sample.

① Determination of Paclitaxel Concentration in Blood (HPLC Method)

Plasma was obtained by centrifuging collected blood for 10 min at 3000 rpm and stored at −20° C. until being analyzed. Into 200 μl of plasma, 10 μl of butyl-p-hydroxybenzoic acid solution dissolved in acetonitril at 100 μg/ml was added as an internal standard. The sample was extracted by adding 1 ml tert-butylmethylether and vortexed for 30 seconds. To separate the organic layer, the above solution was centrifuged for 5 min at 3000 rpm, and 0.8 ml of the organic layer was taken out and dried under the stream of nitrogen atmosphere. The residue was dissolved in 80 μl of 60% acetonitril. Thirty microliters of the above sample was injected into HPLC to analyze the concentration of paclitaxel. HPLC system consists of Shisheido Nanospace Semimicro Column HPLC, SI-1/2001 pump, SI-1/2002 UV-VIS detector, SI-1/2004 column oven, SI-1/2003 autosampler, SI-1/2009 degassing unit, SI-1/2011, 2012 rotary high pressure 6-way valve and Shisheido-MicroChrom software. CAPCELPAK MF Ph-2 cartridge (4.6×20 mm) was used as pre-treatment column, and separation of compounds was achieved using a CAPCELL PAK C18 UG120 (2.0×250 mm) concentrating column. Mobile phase was 50% phosphate buffer solution (0.1%, pH=6.86) (pump A) and 50% acetonitril (pump B), and column temperature was maintained at 30° C. Paclitaxel concentration in blood was analyzed by column switching method. In case of pre-treatment column and analytical column, the flow rates of the mobile phase, 0.1% phosphate buffer/acetonitril solution (84:16 by weight) were 0.5 ml/min and 0.1 ml/min, respectively.

The switching valve was set to A position to dispose of the eluent of the pre-treatment column, and the eluent of the analytical column was allowed to go through the UV detector. Since the internal standard and paclitaxel were detected at 4.1~7.2 min and 6.4~9.3 min, respectively, after going through the pre-treatment column, switching valve was set to B position at 4.0 min to allow the eluent of the pre-treatment column to go through the concentrating column. At 10 min, the switching valve was set to A position again, to change the flow from the concentrating column to analytical column. The chromatograms were collected at 227 nm and analyzed by using Syscon software (Shisheido).

Figure 5:
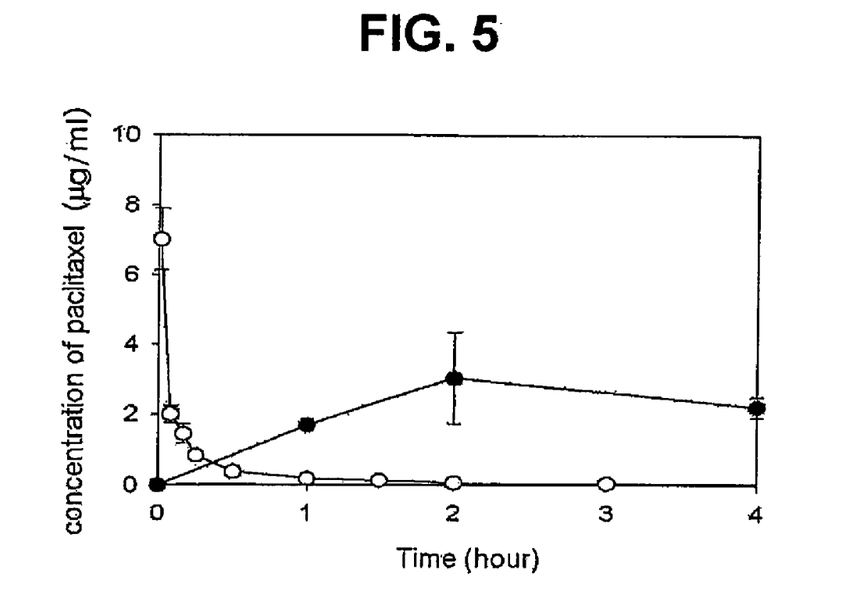
FIG. 5 is a graph showing the concentration of paclitaxel in blood after oral administration of the oily composition containing emulsifier (weight ratio of the composition is monoolein:tricaprylin:Tween 80:paclitaxel=55:28:16:1). The quantitative analysis of total concentration of paclitaxel was performed by HPLC. Taxol® of Bristol-Myers Squibb Company was administered intravenously as a control group.
—●—; a group orally administered with liquid formulation containing emulsifier for solubilization of paclitaxel of the present invention (1 mg paclitaxel), and
—○—; a group intravenously administered with Taxol® of Bristol-Myers Squibb company (40 μg paclitaxel).

② Oral Administration of Composition for the Solubilization of Paclitaxel Including Emulsifier The composition for solubilizing paclitaxel including emulsifier prepared in Example 3 containing 1 mg paclitaxel were administered into Balb/C mouse by using identical method as in Example 12. As a control for oral administration, Taxol® of Bristol-Myers Squibb Company was administered intravenously into Balb/C mouse (6~7 weeks old, female), and the concentration of paclitaxel in blood was determined for 4 hours. After dispersing 0.4 ml of Taxol® in 5.6 ml water, 0.1 ml of the dispersion (corresponding to 40 μg of paclitaxel) was administered by bolus injection into the tail vein of Balb/C mouse fasted for 4 hours. Blood was collected from the eye up to 4 h after the administration of the compositions, the concentration of paclitaxel in the collected blood was determined. Paclitaxel concentration was determined by HPLC as shown in FIG. 5. The bioavailability upon oral administration of composition for the solubilization of paclitaxel including emulsifier when compared to the bolus injection was approximately 30.3%.

Example 18

Figure 6:
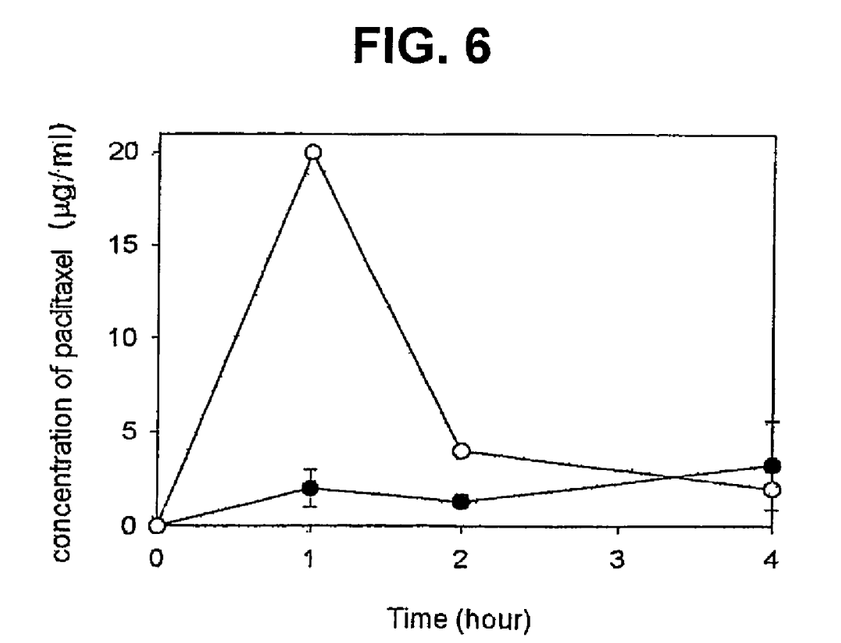
FIG. 6 is a graph showing the total concentration of paclitaxel and its metabolites in blood after intraperitoneal or intramuscular administration of the liquid formulation containing emulsifier in the composition of Example 3. The quantitative analysis of total concentration of paclitaxel and its metabolites was performed by ELISA.
—●—; a group intraperitoneally administered with liquid formulation containing emulsifier for solubilization of paclitaxel of the present invention (1 mg paclitaxel monoolein:tricaprylin:Tween 80:paclitaxel=55:28:16:1, the composition in Example 3),
—○—: a group intramuscularly administered with liquid formulation containing emulsifier for solubilization of paclitaxel of the present invention (1 mg paclitaxel, weight ratio of the composition is monoolein:tricaprylin:Tween 80:paclitaxel=55:28:16:1, the composition in Example 3)

In Vivo Intraperitoneal Administration of Composition for Solubilization of Paclitaxel Including Emulsifier Fifty microliters of the composition for solubilizing paclitaxel including emulsifier prepared in Example 3 containing 1 mg paclitaxel was administered into Balb/C mouse via intraperitoneal administration. The total concentrations of paclitaxel and its metabolites in blood with time are determined by ELISA as shown in FIG. 6.

Example 19

In Vivo Intramuscular Administration of Composition for Solubilization of Paclitaxel Including Emulsifier Fifty microliters of the composition for solubilizing paclitaxel including emulsifier prepared in Example 3 containing 1 mg paclitaxel were administered into Balb/C mouse via intramuscular administration. The total concentrations of paclitaxel and its metabolites in blood with time are determined by ELISA as shown in FIG. 6.

INDUSTRIAL APPLICABILITY

As described above, the composition for solubilizing paclitaxel according to the present invention can solubilize paclitaxel stably and also does not form precipitates of paclitaxel when dispersed in water. Also in aqueous environment, the composition forms unstable dispersion of particles of 30 nm~5 μm. Paclitaxel concentration in blood can be maintained for more than 4 hours when the composition for solubilizing paclitaxel according to the present invention is delivered via oral, intraperitoneal and intramuscular administration.

The invention claimed is:
1. A solubilized paclitaxel composition consisting of:
   1) 40 to 89.9% by weight of monoolein;
   2) 10 to 59.99% by weight of an oil chosen from triglyceride, iodized oil, vegetable oil and animal oil; and
   3) 0.01 to 10% by weight of paclitaxel,
   said % by weight being based on the total weight of the composition.
2. A solubilized paclitaxel composition consisting of:
   1) 40 to 89.9% by weight of monoolein;
   2) 10 to 59.99% by weight of an oil chosen from triglyceride, iodized oil, vegetable oil and animal oil; and
   3) 0.01 to 10% by weight of paclitaxel; and
   4) 0.01 to 5% by weight of additive,
   said % by weight being based on the total weight of the composition,
   wherein the additive is selected from the group consisting of an anticancer drug, a p-glycoprotein inhibitor and a hepatic metabolism blocker.
3. A solubilized paclitaxel composition consisting of:
   1) 40 to 89.9% by weight of monoolein;
   2) 10 to 59.99% by weight of an oil chosen from triglyceride, iodized oil, vegetable oil and animal oil;
   3) 0.01 to 10% by weight of paclitaxel; and
   4) 0.01 to 90% by weight of at least one emulsifier,
   said % by weight being based on the total weight of the composition.
4. The solubilized paclitaxel composition according to any one of claims 1 to 3,
   wherein said triglyceride is chosen from saturated and unsaturated triglycerides having 2 to 20 carbon atoms in each hydrocarbon chain.
5. The solubilized paclitaxel composition according to any one of claims 1 to 3,
   wherein said triglyceride is chosen from triacetin, tributyrin, tricaproin, tricaprylin, tricaprin and triolein;

wherein said iodized oil is chosen from Lipiodol, iodized poppy seed oil, Ethiodol and iodized soybean oil;

wherein said vegetable oil is chosen from soybean oil, cottonseed oil, olive oil, poppyseed oil, linseed oil and sesame oil; and wherein said animal oil is chosen from squalane and squalene.

6. The solubilized paclitaxel composition according to any one of claims 1 to 3, wherein the composition is suitable for oral administration, buccal administration, mucosal administration, intranasal administration, intraperitoneal administration, subcutaneous injection, intramuscular injection, transdermal administration, or intratumoral injection.

7. The solubilized paclitaxel composition according to any one of claims 1 to 3, wherein the composition is liquid or semi-solid state at room temperature.

8. The solubilized paclitaxel composition according to claim 2, wherein the anticancer drug is chosen from doxorubicin, cisplatin, carboplatin, carmustin (BCND), dacarbazine, etoposide, 5-fluorouracil and a paclitaxel derivative chosen from docetaxel, bromotaxel and taxotere; wherein said p-glycoprotein inhibitor is chosen from cinchonin, a calcium channel blocker, a calmodulin antagonist, an antihypertensive, a Vinca alkaloid, a steroid, an antiarrhythmic, an anthelmintic and an immunosuppressant; and wherein said hepatic metabolism blocker is chosen from an anticancer drug chosen from cyclosporin A, doxorubicin, etoposide (VP-16) and cisplatin, verapamil and tamoxifen.

9. The composition for solubilization of paclitaxel according claim 8, wherein the calcium channel blocker is chosen from verapamil and a dihydropyridine chosen from nifedipine, nicardipine and nitrendipine; wherein the calmodulin antagonist is chosen from trifluoroperazine; wherein the antihypertensive is reserpine; wherein the Vinca alkaloid is chosen from vincristine and vinblastine; wherein the steroid is progesterone; wherein the antiarrhythmic is chosen from amiodarone and quinidine; wherein the anthelmintic is chosen from quinacrine and quinine; and wherein the immunosuppressant is chosen from cyclosporine A, staurosporine and tacrolimus.

10. The solubilized paclitaxel composition according to claim 3, wherein said emulsifier is chosen from a phospholipid, a non-ionic surfactant, an anionic surfactant, a cationic surfactant and bile acid.

11. The solubilized paclitaxel composition according to claim 10, wherein said phospholipid is chosen from a phosphatidylcholine (PC) and its derivative, a phosphatidylethanolamine (PE) and its derivative, a phosphatidylserine (PS) and its derivative, and a polymeric lipid wherein a hydrophilic polymer is conjugated to the lipid headgroup;

wherein said non-ionic surfactant is chosen from a poloxamer (polyoxyethylene-polyoxypropylene copolymer), a sorbitan ester (sorbitan esters), a polyoxyethylene sorbitan and a polyoxyethylene ether;

wherein said anionic surfactant is chosen from a phosphatidylserine (PS) and its derivative, a phosphatidic acid (PA) and its derivative, and sodium dodecyl sulfate (SDS);

wherein said cationic surfactant is chosen from 1,2-dioleyl-3-trimethylammonium propane (DOTAP), dimethyldioctadecylammonium bromide (DDAB), N-[1-(1,2-dioleyloxy)propyl]-N,N,N-trimethylammonium chloride (DOTMA), 1,2-dioleyl-3-ethylphosphocholic acid (DOEPC) and 3β-[N[(N',N'-dimethylamino)ethan] carbarnoyl] cholesterol (DC-Chol); and wherein said bile acid is chosen from cholic acid, its salt and derivatives; deoxycholic acid, its salt and derivatives; chenocholic acid, its salt and derivatives; and lithocholic acid, its salt and derivatives.

12. The solubilized paclitaxel composition according to claim 1, wherein the solubilized paclitaxel composition is an oral formulation.

13. The solubilized paclitaxel composition according to claim 2, wherein the solubilized paclitaxel composition is an oral formulation.

14. The solubilized paclitaxel composition according to claim 3, wherein the solubilized paclitaxel composition is an oral formulation.

15. The solubilized paclitaxel composition according to claim 1, wherein said oil is triglyceride.

16. A method of preparing the composition for solubilization of paclitaxel according to claim 1, wherein said method comprises the steps of:

(1) solubilizing 40 to 89.9% by weight of monoolein in 10 to 59.9% by weight of an oil chosen from triglyceride, iodized oil, vegetable oil and animal oil; and (2) solubilizing completely 0.01 to 10% by weight of paclitaxel in said mixture in step (1) by stirring, said % by weight being based on the total weight of the composition.

* * * * *